United States Patent [19]

Dickenson et al.

[11] Patent Number: 5,409,768

[45] Date of Patent: Apr. 25, 1995

[54] MULTICOMPONENT NONWOVEN FIBROUS WEB

[75] Inventors: F. Lee Dickenson; Frank P. Abuto, both of Alpharetta; Leon E. Chambers, Jr., Cumming, all of Ga.; Edward E. Werner, Oshkosh; Tony J. Wisneski, Kimberly, both of Wis.

[73] Assignee: Kimberly-Clark Corporation, Neenah, Wis.

[21] Appl. No.: 224,602

[22] Filed: Apr. 7, 1994

Related U.S. Application Data

[60] Continuation of Ser. No. 90,840, Jul. 12, 1993, abandoned, which is a division of Ser. No. 945,442, Sep. 14, 1992, Pat. No. 5,227,107, which is a continuation of Ser. No. 564,016, Aug. 7, 1990, abandoned.

[51] Int. Cl.$^6$ .......................... B32B 5/08; B32B 5/26; D04H 1/70; D04H 5/08
[52] U.S. Cl. .................................. 428/283; 428/286; 428/298; 428/303; 604/377; 604/378; 604/385.1
[58] Field of Search ............... 428/283, 286, 298, 303

[56] References Cited

U.S. PATENT DOCUMENTS

| | | |
|---|---|---|
| 2,357,392 | 9/1944 | Francis, Jr. . |
| 2,464,301 | 3/1949 | Francis, Jr. . |
| 2,483,405 | 10/1949 | Francis, Jr. . |
| 2,483,406 | 10/1949 | Francis, Jr. . |
| 2,950,752 | 8/1960 | Watson et al. . |
| 2,953,187 | 9/1960 | Francis, Jr. . |
| 2,988,469 | 6/1961 | Watson . |
| 3,073,735 | 1/1963 | Till et al. .......................... 156/38 |
| 4,100,324 | 7/1978 | Anderson et al. ................ 428/288 |
| 4,334,637 | 6/1982 | Baker et al. .................... 222/146 H |
| 4,429,001 | 1/1984 | Kolpin et al. ...................... 428/283 |
| 4,590,114 | 5/1986 | Holtman ............................ 428/171 |
| 4,604,313 | 8/1986 | McFarland et al. ............... 428/172 |
| 4,610,678 | 9/1986 | Weisman et al. .................. 604/368 |
| 4,650,479 | 3/1987 | Insley ................................ 604/358 |
| 4,655,757 | 4/1987 | McFarland et al. ............... 604/366 |
| 4,724,114 | 2/1988 | McFarland et al. ............... 264/510 |
| 4,755,178 | 7/1988 | Insley et al. ...................... 604/367 |
| 4,767,586 | 8/1988 | Radwanski et al. ............... 264/113 |
| 4,773,903 | 9/1988 | Weisman et al. .................. 604/368 |
| 4,785,996 | 11/1988 | Ziecker et al. ................... 239/298 |
| 4,865,596 | 9/1989 | Weisman et al. .................. 604/368 |
| 4,891,249 | 1/1990 | McIntyre .......................... 427/421 |
| 4,904,439 | 2/1990 | Farrington et al. ............... 264/510 |
| 4,915,897 | 4/1990 | Farrington et al. ............... 264/517 |
| 4,927,346 | 5/1990 | Kaiser et al. ..................... 425/81.1 |
| 4,927,582 | 5/1990 | Bryson ............................. 264/113 |
| 4,931,357 | 6/1990 | Marshall et al. .................. 428/284 |
| 5,227,107 | 7/1993 | Dickenson et al. ............... 264/113 |

FOREIGN PATENT DOCUMENTS

| | | |
|---|---|---|
| 296279 | 12/1988 | European Pat. Off. . |
| 307967 | 3/1989 | European Pat. Off. . |
| 399511 | 11/1990 | European Pat. Off. . |

Primary Examiner—James C. Cannon
Attorney, Agent, or Firm—Patrick C. Wilson

[57] ABSTRACT

The present invention relates to a multicomponent fibrous nonwoven structure and the process and apparatus for producing the same. More specifically, the present invention relates to a process for forming nonwoven materials using a forming chamber in conjunction with multiple fiber sources and a forming surface to create multicomponent nonwoven materials with varying features. The materials so produced are suitable for use in a wide variety of applications including personal care products such as diapers, feminine pads and adult incontinence products.

9 Claims, 7 Drawing Sheets

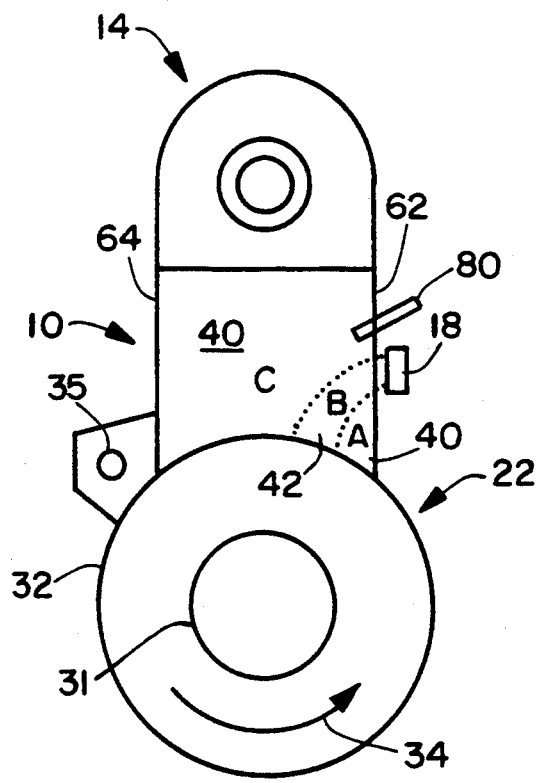
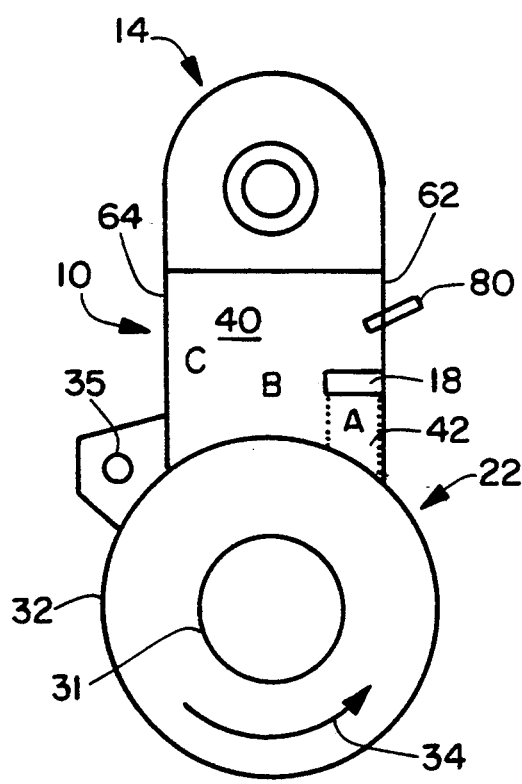
FIG. 17      FIG. 19
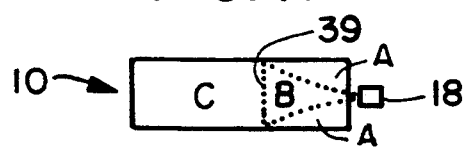
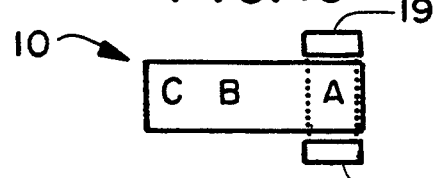
FIG. 18      FIG. 20

MULTICOMPONENT NONWOVEN FIBROUS WEB

This application is a continuation of Ser. No. 08/090,840, filed Jul. 12, 1993 and now abandoned, which is a division of Ser. No. 07/945,442, filed Sep. 14, 1992 and now U.S. Pat. No. 5,227,107, which is a continuation of Ser. No. 07/564,016, filed Aug. 7, 1990 and now abandoned.

BACKGROUND OF THE INVENTION

The present invention relates to a multicomponent fibrous nonwoven structure and the process and apparatus for producing the same. More specifically, the present invention relates to a process for forming nonwoven materials using a forming chamber in conjunction with multiple fiber sources and a forming surface to create multicomponent nonwoven materials with varying features. The materials so produced are suitable for use in a wide variety of applications including personal care products such as diapers, feminine pads and adult incontinence products.

The developments in nonwoven technology have made tremendous strides over the past two to three decades. Today there exists a wide variety of technologies for forming nonwoven materials. Examples of such technologies include meltblowing, spunbonding, meltspinning, solution spinning, carding, meltspraying and wet/dry air laying. Many of these technologies are used individually to form single component materials. As an example, spunbonding is used to form nonwoven materials which can be used in such articles as work wear and personal care products including diapers. Meltblowing can be used to generate fine pore structures adaptable for such uses as filter media and absorbents for oil and other liquids. Air laying can be used to form such products as fibrous wood pulp batts for use as absorbents in diapers and sanitary napkins. In all such cases a particular technology is used to create the particular item.

In addition to single technology materials, various technologies can be combined to create multicomponent materials. An example of this is a spunbond/meltblown/spunbond material such as disclosed in the commonly assigned patent to Brock, et al. (U.S. Pat. No. 4,100,324). This material is generally regarded as a laminate which has found uses in a wide number of areas including wipers, surgical gowns and surgical draping. In still other applications, certain technologies are combined to bring the advantages of two different forming technologies into one product. An example of such a material is described in the commonly assigned patent to Anderson, et al. (U.S. Pat. No. 4,100,324) which describes what is referred to as a coform material. This material is a combination of wood pulp fluff and meltblown fibers which are added to the fluff mixture from ancillary sidestreams as the fluff is deposited onto a forming surface such as a foraminous wire. All of these technologies and their combinations while having particular advantages also have certain disadvantages and limitations. It is therefore an object of the present invention to provide a new process and apparatus for forming nonwovens made from combinations of various technologies.

One area where the present invention is particularly well suited is with respect to the generation of fluid absorbent materials which include wood pulp fluff as one of the components. The mechanical stress and fluid handling requirements of absorbent products sometimes require the presence of bonding agents, adhesives or entangled fibers within the absorbent core to provide integrity to the product as well as to deliver and maintain the fluid functionality benefits. Anderson et al. (U.S. Pat. No. 4,100,324) teaches a method of uniformly mixing meltblown fibers in a fiberized pulp stream to produce a coform web which possesses greater strength and less dusting than pure pulp. Insley (U.S. Pat. No. 4,755,178) and Weisman (U.S. Pat. No. 4,773,903) also teach methods to produce mixed products containing blown fibers which are used to entangle other fibers or particulate materials. The addition of the meltblown fibers adds integrity to the fluff structure, however, the problem with producing this type of structure is that the material must be made on a base machine. Once the material is made, it must be slit, rewound and then transported to a mill to be converted into a finished product such as a diaper, feminine pad or incontinence garment. This activity can have an adverse effect upon the formed web simply due to the handling and processing of the finished roll. Furthermore, a high level of meltblown material within the web is generally needed to hold the structure together so that it can survive the trimming, transporting and converting operations. In addition, forming off line can result in waste due to the trimming process which is unavoidable due to the lack of control in the formation process itself. It is therefore another object of the present invention to provide a process which will reduce the aforementioned problems. The present invention provides a way to add continuous thermoplastic fibers to an absorbent composite web directly on a converting line thereby bypassing the trimming, rewinding, slitting and transportation steps. In addition, lesser quantities of the reinforcing fibers can be utilized in the finished product because the composite web is immediately converted into a finished product and therefore does not have to withstand the rigors of transportation and processing as previously mentioned.

Another problem for certain formation processes involving wood pulp fluff absorbents stems from the need for high reinforcing fiber contents or the use of adhesives throughout the material to provide sufficient integrity. In either case such additions limit the ability to scarf the absorbent to contour or shave its exterior design. It is therefore an object of the present invention to provide a process for forming materials with integrity properties and which can still be scarfed. This is possible with the present process due to the fact that the integrity fibers can be strategically placed within localized regions of the material away from the scarfing roll, thereby providing sufficient integrity while also permitting scarfing to contour the exterior surface of the material.

Another disadvantage with certain forming processes for creating wood pulp fluff absorbent batts is the degree of dusting that occurs when forming, transporting and handling the wood pulp and resultant batt. The dusting results in wasted product as well as posing an additional cleaning problem for the work place, It is therefore an object of the present invention to provide a process which is cleaner from an operational standpoint. This is accomplished at least in part: because the present process utilizes a forming chamber which contains and directionally locates the fiberized wood pulp within a discrete area. The use of such a forming chamber allows for a reduction in the amount of dusting through the deposition of the material at discrete locations either on a forming surface or directly within the intended overall product.

Yet a further object of the present invention is to provide a process which will permit the addition of further components, such as particulate matter, within an environment which is well contained due to the use of a forming chamber. While the above advantages are primarily directed to the utilization of the present process to form reinforced absorbent materials, the process is also suitable for combining multiple components including other fiber technologies such as staple fibers, continuous and noncontinuous fibers, adhesives and particulate matter to form a wide variety of materials. In addition, the process of the present invention will permit the generation of materials which have localized regions containing various fractions or mixtures of the component materials. The advantages outlined above as well as other advantages will become more apparent upon a further review of the following specification, drawings and claims.

SUMMARY OF THE INVENTION

The present invention relates to a multicomponent fibrous nonwoven structure and the process and apparatus for producing the same. More specifically, the present invention relates to a process for forming nonwoven materials using a forming chamber in conjunction with multiple fiber sources and a forming surface to create multicomponent nonwoven materials with varying features. The materials so produced are suitable for use in a wide variety of applications including personal care products such as diapers, feminine pads and adult incontinence products.

The apparatus portion of the present invention includes a first fiber source and a second fiber source both of which are used to direct their respective fibers into a forming chamber. Depending upon the regions into which the fibers are deposited within the forming chamber, mixture of the fibers may or may not take place before the fibers are deposited onto a forming surface. As a result, a wide variety of multicomponent nonwoven materials can be made. Furthermore, the number of variations in materials can be increased by adding additional fiber sources as well as particulate materials and adhesives.

A single layer two component material can be made by directing the fibers from the first and second fiber sources throughout the forming chamber such that they mix to form a relatively uniform fibrous precursor which is then deposited from the forming chamber onto a forming surface such that a fibrous nonwoven web is made which is a mixture of the first and second fibers.

To form more complex materials with regions or layers having different combinations of fibers it is best to describe the interior of the forming chamber as having a series of regions along the machine direction of the forming chamber. Specifically, the chamber can be viewed as having a leading region and a trailing region laterally separated by a central region. The first fibers are introduced into the forming chamber through a fiber inlet such that the first fibers are dispersed within the leading, trailing and central regions. Next, a plurality of second fibers are introduced into the leading region of the forming chamber via the second fiber source such that a fibrous precursor to the nonwoven web is formed. This fibrous precursor is then deposited onto a forming surface via a fiber outlet in the forming chamber to form a fibrous nonwoven web having a first region or layer comprising a mixture of the first and second fibers and a second region or layer comprised predominately of the plurality of first fibers.

By altering the region into which the second fibers are introduced, several other materials can be formed. For example, the reverse of the previously described two region material can be formed by switching the introduction of the second fibers from the leading to the trailing region. In so doing, a fibrous nonwoven web is formed which has a first region comprised predominately of the plurality of first fibers and a second region comprised of a mixture of both the first and second fibers.

It is also possible to form three region fibrous nonwoven materials. One way to do this is by introducing the plurality of second fibers into the central region of the forming chamber while the first fibers are dispersed throughout all three regions.. The result is a fibrous precursor which, when deposited from the fiber outlet onto a forming surface, yields a fibrous nonwoven web with a first region comprised predominately of the plurality of first fibers, a second region which comprises a mixture of the first and second fibers, and a third region comprised predominately of the plurality of first fibers.

A third fiber source can also be introduced into the forming chamber with the third fiber source generating fibers that are either the same as or different than the fibers produced by the first and second fiber sources. For example, it is possible to introduce the first fibers within the leading, trailing and central regions while the second fibers are introduced into the leading region and the third fibers are introduced into the trailing region. The fibrous nonwoven web that results has a first region comprised of a mixture of the first and second fibers, a second region comprised predominately of the first fibers and a third region comprised of a mixture of the first and third fibers.

If the spray pattern of the second fibers is extended such that it extends into both the leading region and a portion of the central region and likewise the spray pattern of the third fibers is extended into both the trailing region and a portion of the central region, then yet another material will be created. By using this configuration of fiber deposition, a fibrous nonwoven web material is created which has a first region comprised of a mixture of first and second fibers, a second or middle region which is comprised of a mixture of all three fibers and a third region which is a mixture of the first and third fibers.

With all the foregoing embodiments of the present invention it is possible to add yet further constituents such as, for example, superabsorbents and adhesives. Such materials can be added within the chamber to one or more of the regions. Alternatively, these materials can be added to the nonwoven outside the forming chamber before or after the fibrous precursor has been deposited onto the forming surface.

The materials, process and apparatus of the present invention can be used directly on a converting line to form nonwoven materials within an overall process such as the generation of personal care products including diapers, sanitary napkins and incontinence garments. As a result, it is possible to utilize the process of the present invention in a continuous manner or alternatively, one or more of the components can be cycled or pulsed on and off to create localized zones of the particular material being pulsed. For example, if the material being made is a reinforced superabsorbent fluff composite for a diaper, either or both of the second fibers and superabsorbent may be cycled on and off to create localized regions of the cycled material.

BRIEF DESCRIPTION OF THE DRAWINGS

FIG. 17 is a schematic side view of the apparatus and process according to the present invention including a first fiber source which deposits fibers into the leading, trailing and central regions, a second fiber source and a forming drum as opposed to the forming wire in the previous drawings with the second fiber source introducing its fibers into the central region of the forming chamber.

FIG. 18 is a schematic top plan view of the forming chamber and second fiber source according to the present invention along with the spray pattern of the second fiber source.

FIG. 19 is a schematic side view of the apparatus and process according to the present invention.

FIG. 20 is a schematic top plan view of the forming chamber, second fiber source and third fiber source according to the present invention with the spray patterns of the second and third fiber sources as they introduce their fibers into the leading region of the forming chamber.

DETAILED DESCRIPTION OF THE INVENTION

The present invention relates to a process for forming multicomponent nonwoven materials. For purposes of illustration, the present invention will be described in conjunction with the formation of reinforced absorbent fluff batts containing mixtures of wood pulp fibers and essentially continuous polymeric reinforcing fibers. This should not be considered as a limitation to the present invention, as the process of the present invention is suitable for use with a wide variety of fiber sources and formation processes as well as the addition of other components such as adhesives and particulate matter.

Figure 1:
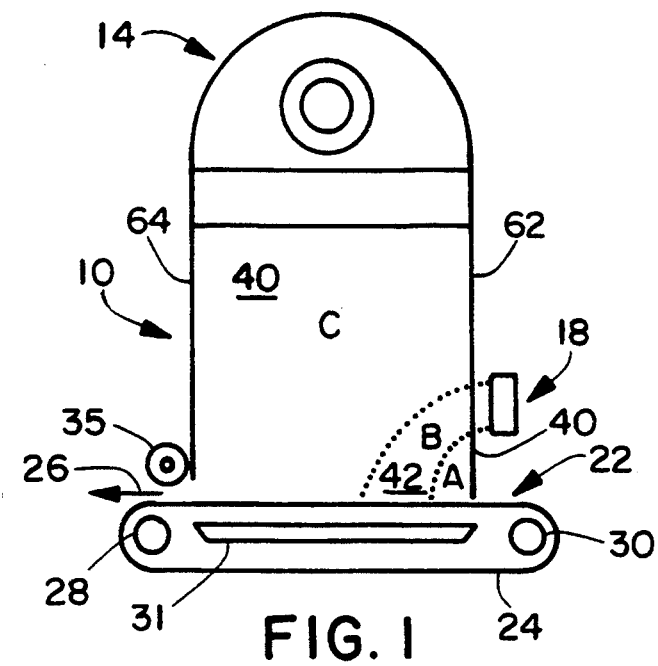
FIG. 1 is a schematic side view of the apparatus and process according to the present invention including a first fiber source which deposits fibers into the leading, trailing and central regions and a second fiber source which introduces its fibers into the central region of the forming chamber.

Referring to FIG. 1, in the most general terms the equipment for the present process includes a forming chamber 10, a first fiber source 14, a second fiber source 18 and a collection or forming surface 22. As depicted in FIG. 1, the forming surface 22 is in the form of a continuous loop foraminous wire 24 which travels in the direction of arrow 26. Alternatively, as is shown in FIGS. 17 and 19, the collection/forming surface 22 may take the form of a rotating drum 32 which rotates in the direction of arrow 34. The forming surface 22 as shown in FIG. 1 is a foraminous wire 24 which travels in the direction of arrow 26 about a pair of rollers 28 and 30, either one or both of which may be driven. If desired, the speed of the wire 24 can be variably driven so the line speed of the wire 24 can be controlled in relation to the deposition rates of the first and second fiber sources 14 and 18, respectively. The motion of the wire 24 can also be cycled on and off if desired.

To further facilitate fiber lay down onto the wire 24, a vacuum assist 31 may be located underneath the wire 24 to draw the fibers down onto the forming surface 24. The amount of vacuum can be varied or turned off to meet the specific needs of the material being formed.

Figure 4:
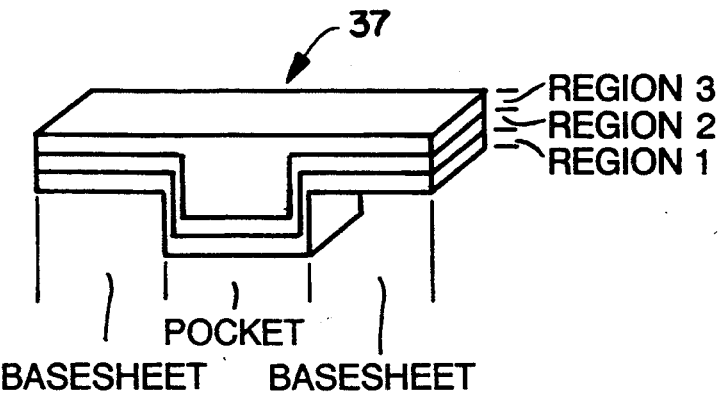
FIG. 4 is a perspective view of a contoured and scarfed three region nonwoven material according to the present invention.

Certain cases may require that the fibrous nonwoven material be contoured in shape or shaved to reduce thickness. Giving contour to the material can be effected in one of two ways. The first is to form a relatively uniform material and then shave some of the fibrous material from the batt by using a scarfing roll 35 as shown in FIGS. 1, 5, 17 and 19. This creates waste material which must either be recycled or discarded. The second way is to use a forming wire 24 which is, itself, contoured in shape so that the nonwoven formed thereon takes the shape of the forming wire 24. Alternatively, contouring and scarfing can be used together. An example of such a contoured material is shown in FIG. 4. As can be seen, the absorbent material 37 has a thicker middle section and thinner sides thereby concentrating the bulk of the absorbent capacity of the material in the middle of the product as for use in a diaper or incontinence construction.

An alternate collection/forming surface 22 is a rotating drum 32 as is shown in FIGS. 17 and 19. The rotating forming drum 32 is foraminous so it too can be supplied with a vacuum source to assist in fiber lay down. As with the forming wire 24 in FIG. 1, the forming drum 32 may be contoured or used in conjunction with a scarfing roll 35 to form a contoured structure such as is shown in FIG. 4. Also, the drum speed may be controlled in the same fashion as was described with respect to the forming wire 24, thereby allowing continuous or interrupted formation of nonwoven materials.

Figure 2:
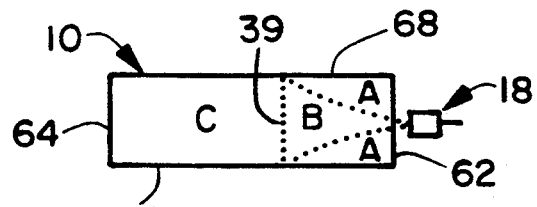
FIG. 2 is a schematic top plan view of the forming chamber and second fiber source according to the present invention along with the spray pattern of the second fiber source.
Figure 3:
FIG. 3 is a side view of a three region nonwoven material according to the present invention formed using the apparatus and process of FIGS. 1 and 2.

Having described the equipment in general terms, the process involves depositing a first plurality of fibers 40 into the forming chamber 10 from the first fiber source 14. As shown in FIG. 1, the first plurality of fibers 40 are generally substantially uniformly deposited throughout the forming chamber 10. At the same time, a second plurality of fibers 42 are deposited within the forming chamber 10 via the second fiber source 18. As with the first fibers 40, the second fibers 42 can be deposited within the forming chamber 10 in a uniform fashion or, instead, they can be deposited into localized regions as in FIG. 1. For purposes of description, the forming chamber 10 can be viewed as being divided into several regions laterally defined in the machine direction of the forming chamber (which coincides with the direction of movement of the forming wire 24 as shown by arrow 26). Again referring to FIG. 1, the forming chamber 10 is divided into a leading region A, and a trailing region C separated by central region B. In FIG. 1, the second fiber source 18 is shown as being positioned such that it deposits its second plurality of fibers 42 substantially within the central region B of the forming chamber 10. (Note that the central region B does not necessarily mean the center of the forming chamber 10 but merely that region which is positioned between the leading region A and the trailing region C). As a result, as the first plurality of fibers 40 and the second plurality of fibers 42 are deposited onto the forming surface 22, a layered structure is achieved which, as shown in cross-section in FIG. 3, has a first region 56 which is adjacent the top of the forming surface 22 and is comprised primarily of the first plurality of fibers 40. This first region 56 is in turn covered with a second region 58 of material which is comprised of a mixture of both the first plurality of fibers 40 and the second plurality of fibers 42. The second region 58 of the material, which corresponds to the fiber formation within the central region B of the forming chamber 10, is in turn covered with a third region of material 60 which is comprised predominately of the first plurality of fibers 40. For purposes of illustration, the cross-section of the material in FIG. 3 can therefore be viewed as having a first region 56 which corresponds to the leading region A, a second region 58 which corresponds to the central region B and a third region 60 which corresponds to the trailing region C. As will be discussed in further detail below, this same explanation as to the process of the present invention can also be readily applied to the apparatus as shown in FIG. 17, the only difference being that the fibers are collected on the forming drum 32 instead of the forming wire 24 shown in FIG. 1. Referring to FIGS. 2 and 18 which are cross-sectional top views of the forming chamber 10, the second plurality of fibers 42 are deposited within the central region B. As with the equipment shown in FIG. 1, the three layer structure, FIG. 3, is accomplished by spraying the second plurality of fibers 42 in a cross-directionally expanding pattern 39. By going from a narrow to wide spray pattern it is possible for the first plurality of fibers 40 to pass around the second plurality of fibers 42 within the leading region A, thereby creating the three layer structure shown in FIG. 3. Depending on how wide the pattern 39 is drawn in the cross-direction, a center or second region 58 of material can be made which is as wide as the overall material by extending the pattern 39 to the side walls of the forming chamber or the width of the region in the material can be made more narrow by retracting the pattern.

Depending upon the localization of the first and second plurality of fibers within the forming chamber, a variety of materials may be formed. Besides allowing the generation of three layer structures, the equipment and process of the present invention will permit the generation of a single layer construction containing a mixture of both the wood pulp fibers and the reinforcing polymeric fibers. In addition, two region materials are possible wherein one region contains a mixture of both the first and second plurality of fibers while the second region contains only one of the two types of fibers. This can be accomplished by directing the second fiber source into either the leading region A or the trailing region C in a more expanded pattern from the outset so that the first fibers 40 cannot pass around the second fibers 42 of the second fiber source 18.

Several types of three region materials are also possible. If the second fiber source 18 is directed within the central region B, a material will result which contains primarily first fibers in the first region 56, a mixture of first and second fibers in the second region 58 and predominately first fibers in the third region 60. By placing a second fiber source in both the leading and trailing regions, another material can be designed which contains mixtures of both the first and second fibers in the first and third regions of the material while the second or middle region contains primarily first fibers. Lastly, by baffling the deposition of the first fiber to fall primarily within the central region while at the same time depositing primarily second fibers in the leading and trailing regions via second fiber sources located in these respective regions, a three region material can be developed which contains two external regions comprised primarily of the second fibers with a central region comprised primarily of the first fibers. Thus, the process and apparatus of the present invention allow the formation of a wide variety of materials. A more detailed description of the equipment, process and products will now ensue.

As shown in FIG. 1, the forming chamber 10 of the present invention is generally rectangular in shape with a width that is usually equal to or less than the forming surface 22 upon which the fibers are deposited. The length of the forming chamber which is generally regarded as the dimension parallel to the machine direction of the forming surface can be varied to meet the dimensions of the equipment and the desired deposition rates of the materials being deposited on the forming surface 22. While the forming chamber shown in the drawings is generally rectangular in shape it should be appreciated that this is not regarded as a restriction and the forming chamber may take any number of shapes consistent with the particular equipment being utilized in the process.

Figure 21:
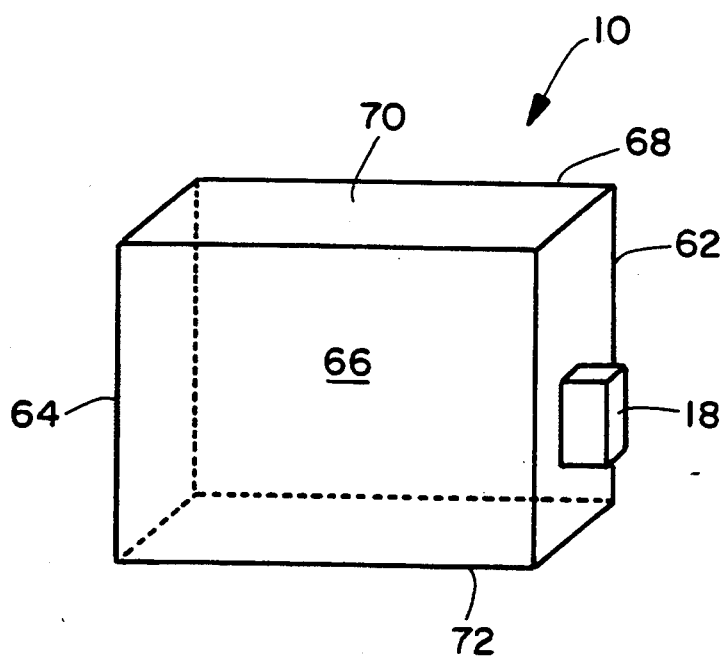
FIG. 21 is a perspective view of a forming chamber and second fiber source according to the present invention.

Referring now to a more detailed depiction of the forming chamber 10 as shown in FIG. 21, the forming chamber 10 has a front side 62 adjacent the leading region A and a back side 64 adjacent the trailing region C separated by two side walls 66 and 68. As shown in Figure 21, the forming chamber 10 has an open top end 70 which is regarded as the fiber inlet and an open bottom end 72 which is regarded as the fiber outlet. Thus as shown in the drawings, the fiber inlet is positioned above the fiber outlet, however, it is also possible to have other configurations such as a fiber inlet below the outlet with the fibers from one of the sources being blown up into the chamber. The forming chamber 10 has a large top opening 70 to accommodate a hammermill or similar fiberizing device which, in the specific examples that follow, serves as the first fiber source 14. The hammermill picks apart a source of absorbent fluff fibers such as from a pulp sheet and deposits them within the forming chamber 10. The fiber outlet 72 is generally as wide as the desired width of the particular product in the cross-direction (CD). Wider forming chamber widths can be used in conjunction with a vacuum 31 underneath the forming wire 24 or drum 32 to draw the fibers inwardly and reduce the actual width of the material thus formed. See FIGS. 1 and 17 for example. The width of the outlet 72 can also be wider than the desired product so that the sides of the material thus formed can be trimmed or so that multiple widths can be made and then slit. The overall height of the forming chamber 10 can be varied to allow greater dispersion or control of the fibers. Generally, the taller the chamber 10, the greater the dispersion of the fibers. The amount of entrainment air used to deposit either or both of the first 40 and second 42 plurality of fibers also should be considered in determining the overall size of the chamber 10. Oftentimes, the height of the chamber will be in the order of a fraction of a meter to several meters with the bottommost edge or outlet 72 being positioned very close to the foraminous wire 24 or the forming drum 32. By keeping the outlet 72 in close proximity to the forming surface 22, the apparatus is more capable of controlling the fiber lay down. When making lofty materials, the back side 64 adjacent the trailing region C of the forming chamber 10 must be sufficiently separated from the top of the forming surface 22 to allow the newly formed nonwoven material to exit the chamber without catching on the wall of the forming chamber 10. Typically the distance between the fiber outlet 72 and the top of the forming surface 22 will be in the order of centimeters.

The first fiber source 14 as shown in FIGS. 1, 5, 8, 11, 14, 17 and 19 is determined by the type of fiber that is desired. In the examples that follow, the first fiber is free-formed cellulose wood pulp (fluff) which is often supplied in roll form and then broken up and fiberized into individual fibers through the use of a hammermill or other known types of fiberizing equipment. In the design shown in the drawings, this fiberizing equipment is placed on top of the forming chamber 10 over the fiber inlet 70 which is very open to accommodate the fibers and the entrainment air supply. Alternatively, the hammermill can be placed elsewhere, as for example, though not shown, to the side of the chamber 10 or below it and the fibers can be blown into the chamber. Note too, that other fibers may be used as the first fiber. Other fibers would include but are not limited to staple fibers, meltblown fibers, spunbond fibers, or fibers formed from adhesives. Each of these other fibers would have their own air source and respective formation equipment which would be readily adapted by one of ordinary skill to mate with the fiber inlet 70 of the forming chamber 10. For purposes of the present application, the term fiber is meant to include particulate material such as, but not limited to, superabsorbents as well as other materials that can be formed as either fibers or particles.

Should the user elect to introduce meltblown fibers into the forming chamber 10 as the first fiber source 14, the meltblown dies could be placed above or in the sides of the chamber 10 to cover one or all of the regions A, B and C. When forming spunbond fibers as the first fiber source, the spunbond equipment would normally be placed on top of the forming chamber due to equipment constraints as to size. With staple fibers other than fluff, the same types of constraints and options would apply as with the introduction of fluff fibers into the chamber. As a result, the staple fibers could be blown in or introduced from above, below or from the sides of the forming chamber 10. Should other fibers and/or materials such as adhesives be sprayed into the chamber, then the actual placement could be varied to locate the equipment within any or all of the leading, trailing or central regions as well as either high or low within the chamber. Still further, it is within the scope of the present invention to invert the equipment and form materials in an upward direction.

Most typically the second fiber source 18 will be an extrudable thermoplastic polymer though other fibers as well as adhesives and particulates can be used. One of the benefits of the present invention is that the design allows for the formation of essentially continuous thermoplastic fibers directly into the forming chamber via compact meltspray equipment as is disclosed in commonly assigned U.S. patent application Ser. No. 07/362,737 entitled "Process and Apparatus For Forming A Nonwoven Web", filed on Jun. 7, 1989 and which is incorporated herein by reference in its entirety. By spraying the continuous thermoplastic fibers directly into the chamber 10, unique and varying properties can be imparted to the overall material due to the localized introduction within a well defined area of the chamber. In so doing, absorbent fluff batts can be made which have a relatively high degree of integrity in view of the low quantities of thermoplastic fiber added to the fluff batt. While any amount of fiber can be added to meet specific end usage needs, typically, significant increases in both wet and dry strength can be achieved through the introduction of thermoplastic fibers in a weight percent as low as 0.10 to 10 percent. However, the percentage of reinforcing fibers may be as high as necessary to meet the end needs of the particular product. Suitable thermoplastic fiber materials would include but are not limited to polyolefins, polyesters, polyamides, poly(ethylene-vinyl acetate), synthetic rubber, adhesive fiber materials, etc.

Turning again to the drawings, because of space constraints, the second fiber source will generally have to be rather compact in nature so that it can be strategically placed within or adjacent to the forming chamber 10 such that the fibers so produced can be directed within the chamber itself. Consequently, if meltblowing or spunbonding technologies are being used, the equipment may have to be downsized in order to fit in combination with the forming chamber 10. On larger production equipment this may not be a problem. However, when utilizing the process and the equipment of the present invention to form materials directly in line as when generating diapers and adult incontinence products, the equipment will most likely have to be very compact. As a result, it may be desirable to use meltspray equipment such as is described in the above-mentioned patent application to Kimberly-Clark entitled "Process and Apparatus For Forming A Nonwoven Web" which has been incorporated herein by reference.

In FIG. 1, the second fiber source 18 is shown being directed into the central region B of the forming chamber 10. The second fibers 42 are directed into the forming chamber 10 such that they fan out from a narrow stream to a broader stream encompassing the width of the chamber 10 such as is shown by the vertical view shown in FIG. 2. As a result, the first fibers 40 are uniformly dispersed throughout the forming chamber 10 while the second fibers 42 mix with the first fibers 40 generally within the central region B thereby forming the composite shown in FIG. 3 which includes a first region 56 and a third region 60 made primarily of the first fibers 40 and a second or central region 58 which separates the first and third regions and is comprised of a mixture of both the first fibers 40 and the second fibers 42. This is due at least in part because of the expanding spray pattern 39 as is shown in FIG. 2. As can be seen, because of the narrow nature of the spray as it enters the forming chamber 10, the first fibers 40 are able to pass around the narrow portion of the spray pattern 39 thereby forming the first region 56 of the material shown in cross-section in FIG. 3. Due to the nature of the apparatus and process, the layer of the formed material which is closest to the forming surface 22 will be that material which first contacts the surface 22 within the leading region A of the forming chamber 10. The first region 56 will be composed primarily of the first fibers, which in the examples, is wood pulp fluff. The second region 58 is where the mixing of the first and second fibers takes place. As a result, the second region 58 will be a mixture of thermoplastic reinforcing fibers and wood pulp fluff. The third region 60 is not contacted by the second fibers 42 and consequently is comprised primarily of the wood pulp fluff fibers.

One of the advantages of the above described process is that a material can be made which does not contain any of the thermoplastic reinforcing fibers (second fibers) 42 within the exterior regions (regions 56 and 60) of the material. As a result, it is possible to use a scarfing roll 35 to contour or shave the exterior surface or surfaces of the newly formed material. This would not be possible if the reinforcing second fibers 42 were uniformly dispersed throughout the entire material. This is because the reinforcing fibers get caught by the scarfing roll and cause the nonwoven batt to be torn apart thereby making the material difficult, if not impossible, to process.

Figure 5:
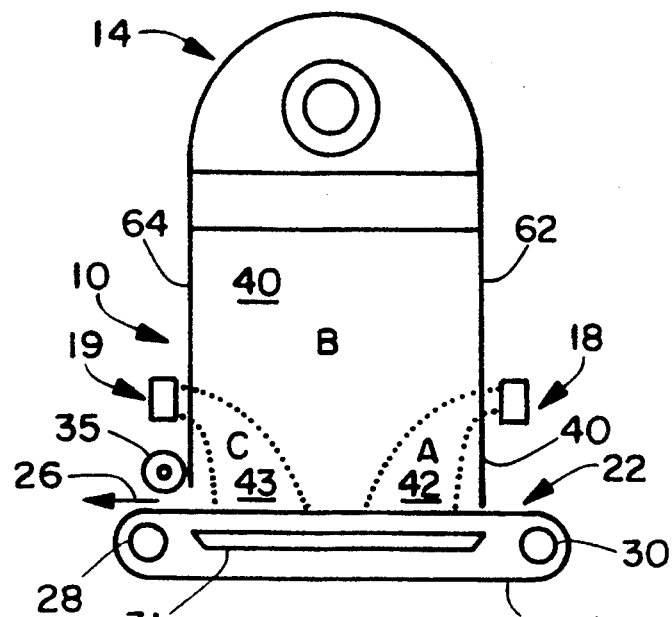
FIG. 5 is a schematic side view of the apparatus and process according to the present invention including a first fiber source which deposits fibers into the leading, trailing and central regions, a second fiber source and a third fiber source with the second fiber source introducing its fibers into the leading region of the forming chamber and the third fiber source introducing its fibers into the trailing region of the forming chamber.
Figure 6:
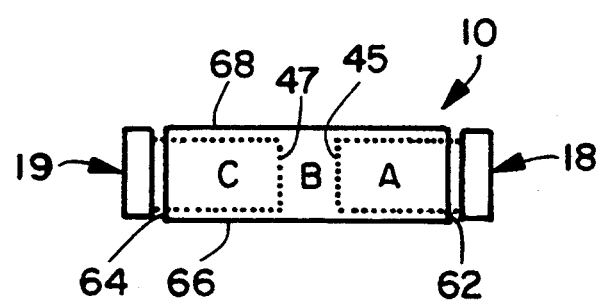
FIG. 6 is a schematic top plan view of the forming chamber, second fiber source and third fiber source according to the present invention along with the spray patterns of the second and third fiber sources.
Figure 7:
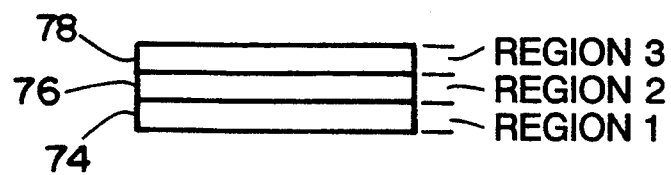
FIG. 7 is a side view of a three region nonwoven material according to the present invention formed using the apparatus and process of FIGS. 5 and 6.

An alternative process to that shown in FIG. 1 for forming nonwovens is shown in FIGS. 5 and 6 with like figure numbers being used for like elements. The primary differences between the process of FIG. 1 and the process of FIG. 5 is the addition of a third fiber source 19 in the back side 64 of the forming chamber 10 adjacent the trailing region C as well as the spray patterns used with respect to the second fiber source 18 and the third fiber source 19. As a result of these changes, a three region material depicted in FIG. 7 is achieved which has a mixture of the first fibers 40 and the second fibers 42 in the first region 74, predominately first fibers 40 in the second region 76 and a mixture of first fibers 40 and third fibers 43 in the third region 78.

In the examples that follow, the third fiber source 19 is the same type of fiber source as that used for the second fibers 42, i.e., continuous thermoplastic reinforcing fibers. Note, however, that this should not be regarded as a limitation as any of the other fiber sources previously listed as possibilities for the first and second fiber sources may also be used for the third fiber source 19.

Another important feature to note with respect to the process shown in FIGS. 5 and 6 as compared to FIGS. 1 and 2 is the spray pattern for the second and third fiber sources 18 and 19, respectively. Unlike the spray pattern 39 in FIG. 2 which starts small and fans out to a width that is approximately that of the forming chamber 10, the spray patterns 45 and 47 from respective fiber sources 18 and 19 more closely approximate the width of the forming chamber 10 from their initial entry into the chamber 10. Consequently, it is more difficult for the first fibers 40 to travel around the spray patterns to create leading and trailing regions, A and C, which are comprised predominately of the first fibers 40. Instead, it is the leading and trailing regions, A and C, wherein the mixing of the various fibers takes place. Lastly, note that it is possible to undertake this same type of formation process on a rotating drum configuration instead of a forming wire.

Figure 8:
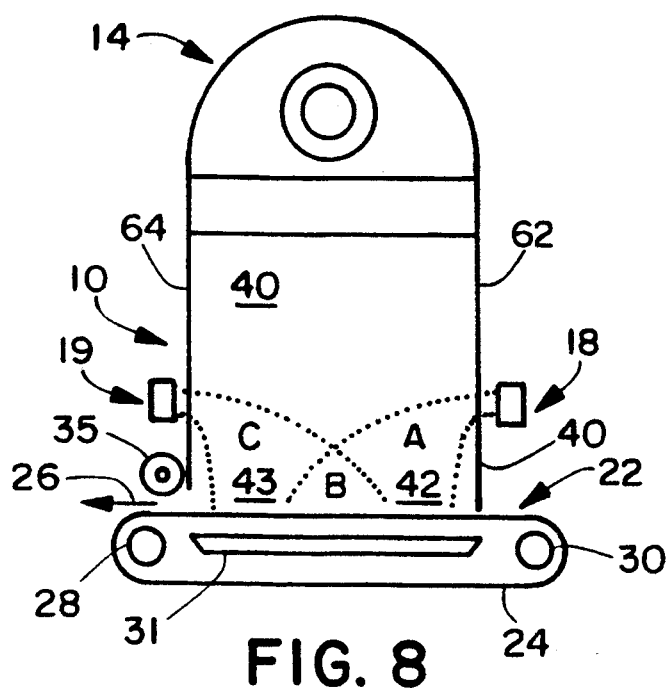
FIG. 8 is a schematic side view of the apparatus and process according to the present invention including a first fiber source which deposits fibers into the leading, trailing and central regions, a second fiber source and a third fiber source with the second fiber source introducing its fibers into the leading region and at least a portion of the central region of the forming chamber and the third fiber source introducing its fibers into the trailing region and at least a portion of the central region of the forming chamber.
Figure 9:
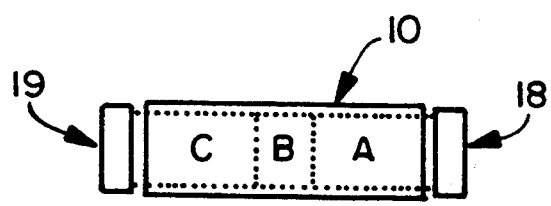
FIG. 9 is a schematic top plan view of the forming chamber, second fiber source and third fiber source according to the present invention along with the spray patterns of the second and third fiber sources.

Another variation of the process according to the present invention is shown in FIGS. 8 and 9. Again, like reference numbers are used for like elements. The process shown in FIGS. 8 and 9 is adapted to yield a nonwoven web material which contains a mixture of fibers throughout the structure. As with the other structures, the first plurality of fibers 40 are introduced into the leading, trailing and central regions of the forming chamber 10 via first fiber source 14. A second plurality of fibers 42 are introduced into the forming chamber 10 via second fiber source 18 and a third plurality of fibers 43 are introduced into the chamber 10 through a third fiber source 19.

The second fiber source 18 is introduced into the front side 62 of the forming chamber 10 such that it covers the leading region A and at least a portion of the central region B. The third fiber source 19 is angled into the back side 64 of the forming chamber 10 such that it covers the trailing region C and at least a portion of the central region B as well as overlapping a portion of the spray from the second fiber source 18, FIG. 8. Both of the fiber sources 18 and 19 in FIG. 9 have spray patterns which more closely approximate the width of the forming chamber 10 as opposed to the expanding spray pattern such as in FIG. 2.

Figure 10:
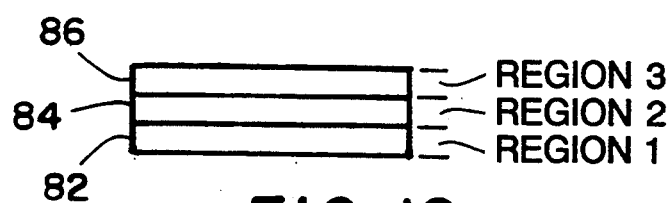
FIG. 10 is a side view of the three region nonwoven material according to the present invention using the apparatus and process of FIGS. 8 and 9.

As a result of the overlapping spray patterns, a material is generated such as is shown in FIG. 10. The first region 82 contains a mixture of first fibers 40 and second fibers 42. The second region 84 contains a mixture of the first fibers 40, second fibers 42 and third fibers 43 while the third region 86 contains a mixture of the third fibers 43 and first fibers 40. Thus, if the second fiber source 18 and the third fiber source 19 inject the same type of fibers into the forming chamber 10, then the material shown in FIG. 10 will have the same two fiber mixture throughout its structure. It is also possible, however, to have the third fiber source 19 introduce a fiber that is different than that introduced by either the first or second fiber sources, 14 and 18. When this happens, the first region 82 and third region 86 have mixtures of two types of fibers while the second region 84 has a mixture of all three types of fibers.

Figure 11:
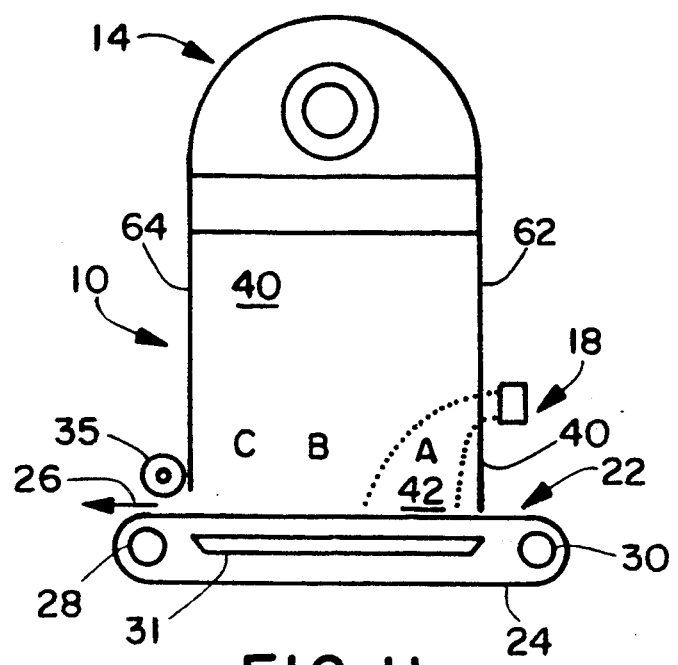
FIG. 11 is a schematic side view of the apparatus and process according to the present invention including a first fiber source which deposits fibers into the leading, trailing and central regions and a second fiber source with the second fiber source introducing its fibers into the leading region of the forming chamber.
Figure 12:
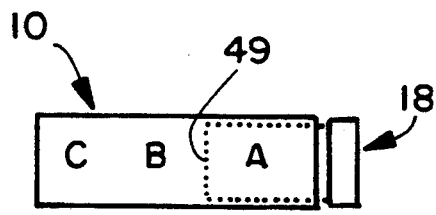
FIG. 12 is a schematic top plan view of the forming chamber and second fiber source according to the present invention along with the spray pattern of the second fiber source.

Yet another variation of the process of the present invention is shown in FIG. 11 and 12. The process is the same as the process shown in FIGS. 1 and 2 except for the spray pattern emitted from the second fiber source 18. Unlike the expanding spray pattern 39 in FIG. 2, the spray pattern 49 in FIG. 12 covers essentially the entire width of the forming chamber 10 from the point of introduction until the point of deposition on the forming wire 24. As a result, a two layer structure (see FIG. 13) is created since it is difficult for the first plurality of fibers 40 to pass around the spray pattern 49 from the fiber source 18 as they are able to within the process shown in FIG. 2. The structure so produced includes a first region 53 formed adjacent the forming wire 24 which is a mixture of the first plurality of fibers 40 and the second plurality of fibers 42. This fiber mixture is deposited primarily within the leading region A of the forming chamber 10. The remainder of the chamber 10 (central region B and trailing region C) only receives deposits of the first fibers 40 and thus the second region 55 of the material shown in FIG. 13 is composed primarily of the first fibers 40.

Figure 13:
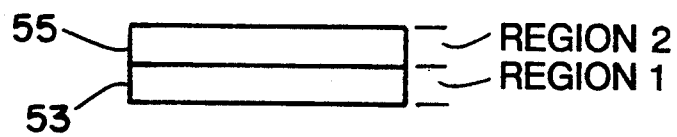
FIG. 13 is a side view of a two region nonwoven material according to the present invention formed using the apparatus and process of FIGS. 11 and 12.
Figure 14:
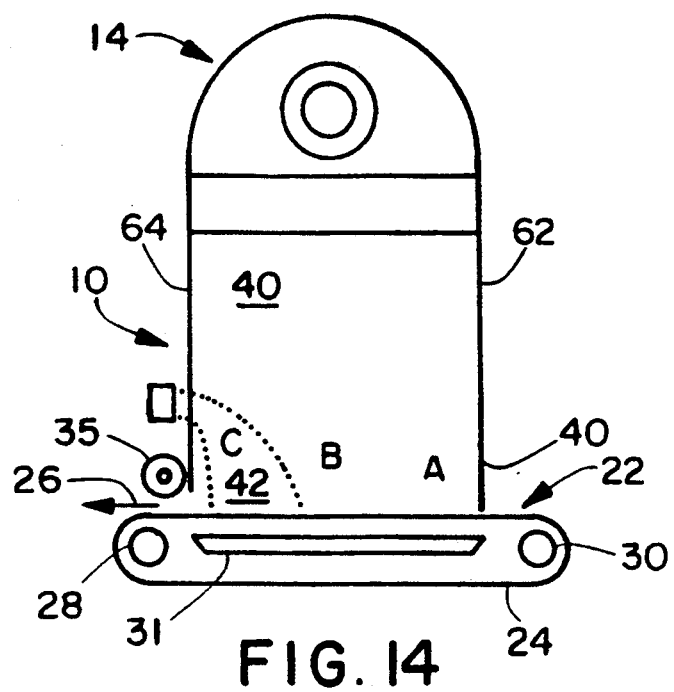
FIG. 14 is a schematic side view of the apparatus and process according to the present invention including a first fiber source which deposits fibers into the leading, trailing and central regions and a second fiber source with the second fiber source introducing its fibers into the trailing region of the forming chamber.
Figure 15:
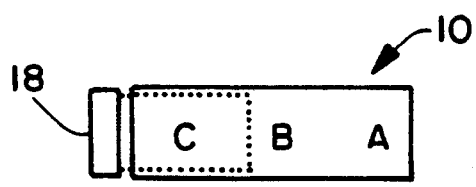
FIG. 15 is a schematic top plan view of the forming chamber and second fiber source according to the present invention along with the spray pattern of the second fiber source.
Figure 16:
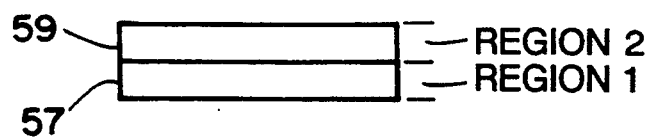
FIG. 16 is a side view of a two region nonwoven material according to the present invention formed using the apparatus and process of FIGS. 14 and 15.

An inverted form of the material shown in FIG. 13 can be created by the process shown in FIGS. 14 and 15 with the cross-section of the resultant material shown in FIG. 16. The difference between this process and the process shown in FIGS. 11 and 12 is the location of the second fiber source 18. In FIGS. 11 and 12 the second fiber source 18 is located in the front side 62 of the forming chamber 10 adjacent the leading region A. In the process shown in FIGS. 14 and 15 the second fiber source 18 is located in the back side 64 of the forming chamber 10 adjacent the trailing region C. As a result, the first region 57 of the material shown in FIG. 16 is composed primarily of the first fibers 40. This is the region adjacent the forming wire 24. The second region 59, which is on top of the first region 57, is composed of a mixture of the first and second fibers, 40 and 42. The advantage of the processes shown in FIGS. 11 and 12 and in FIGS. 14 and 15 is that by moving the second fiber source 18 from one end of the chamber 10 to the other, the location of the region of the material containing the thermoplastic reinforcing fibers can be changed from top to bottom to place the reinforcing fibers in the most advantageous portion of the product. For equipment which has fixed scarfing rolls, this becomes important as its allows the manufacture of a material with the reinforcing fibers away from the scarfing roll so that the equipment does not have to be reworked every time a material includes reinforcing fibers and has to be scarfed.

The process of the present invention will also permit combinations of the various process variables to create yet further nonwoven materials. For example, most of the previous discussion has centered around the use of the second and third fiber sources 18 and 19, within the ends of the forming chamber 10. It is also possible to generate similar materials by locating the fiber sources in the sides, 66 and 68, of the forming chamber and still generate nonwoven materials (see FIG. 19 and the top view of the forming chamber in FIG. 20). If two fiber sources 18 and 19 are located in either of the sides 66 and 68 within the leading region A, a material will be generated that is similar to that shown in FIG. 13.

It is also possible to combine spray patterns as, for example, by using the expanding spray pattern 39, such as is in FIG. 2, in one end of the forming chamber 10 with the uniform spray pattern 49, such as is shown in FIG. 12, in the other end of the forming chamber. Further it is possible to use either the expanding or uniform spray pattern in one or more of the regions. In addition, multiple fiber sources can be used in either the ends, 62 and 64, in the sides, 66 and 68, on top 70 or a combination of the foregoing.

Other materials, including particulate matter such as superabsorbents, may be added. Any suitable means such as an air injection tube 80 as shown in FIGS. 17 and 19 may be used. As with the other components, the location of the particulate material can be varied within the leading region A, central region B, trailing region C or a combination of the foregoing by adjusting the location of the particulate source 80 or sources within the chamber 10. Also note that the particulate material may be pulsed or cycled on and off to create localized zones of the particulate material within the fibrous nonwoven structure.

Lastly, certain equipment, such as the meltspray equipment used as the second fiber source in the following examples may be cycled on and off to create localized regions of material that contain both the first and second fibers as well as localized regions that contain only the first fibers. In material production, this ability to cycle on and off one or more of the components can result in significant cost savings.

The equipment used as the second fiber source within the following Examples uses a technology and apparatus referred to as meltspraying which is disclosed in commonly assign U.S. patent application Ser. No. 07/362,737 entitled "Process and Apparatus For Forming A Nonwoven Web", filed on Jun. 7, 1989 Meltspraying equipment is a compact means for extruding molten polymer into attenuated fibers through the use of one or more high throughput dies which utilize primary and optionally secondary attenuation air to draw the molten polymer into fibers. Another feature of the meltspray equipment is its ability to cycle on and off the production of fibers due to the use of a pneumatic needle valve which is located within the fiber channel.

Generally the apparatus includes a reservoir for supplying a quantity of melted fiber forming thermoplastic polymer resin. The reservoir generally includes means for melting the polymer resin and maintaining the resin in the molten state. Typical resins melt at temperatures in the range of 149° to 260° C. Therefore, the reservoir must be able to maintain resin temperatures within this range. The fiber forming die in its simplest terms can be viewed as having a main housing for receiving a die assembly including a resin nozzle which is included in an air forming chamber and capped with an air plate. The air plate may include a plurality of openings for being seated over a plurality of nozzles. Alternatively, the assemblies may be aligned in a plurality of rows or staggered to increase the number of openings per unit width. The resin nozzles are in turn fitted with retractable plunger assemblies which are a part of the on/off control means and therefore will permit the interruption of resin flow and cleaning of the nozzle orifice. Air is supplied to the die for two uses. The first use is to operate the on/off control means. The second use is to draw or attenuate the molten resin into fibers.

The molten resin first enters the main housing of the die through a resin inlet port which leads into the interior of the nozzle located within the die. The nozzle contains a resin chamber or main flow body which houses and surrounds the hydraulically actuated plunger assembly. Consequently the resin inlet port and main flow body are in fluid communication with one another. As the molten resin enters the main flow body it fills and pressurizes the chamber. The molten resin is then released from the chamber through a resin fluid capillary to form fibers via a resin outlet orifice located within the air plate assembly. Initially the plunger assembly is seated against the base of the resin outlet orifice thereby preventing release of the molten resin. When the plunger is retracted and therefore unseated from the resin outlet orifice, the resin is then permitted to escape from the main flow body and thus begin the formation of the fibers.

To fiberize and attenuate the resin exiting the resin outlet orifice, a fiberization/attenuation air or other fluid is used to surround and draw the resin into fibers. Consequently, the die is equipped with primary and, if desired, secondary fiberization means for drawing and attenuating the fibers. Air or another fluid fiberization source enters the die through a fluid inlet port which is in communication with the air forming chamber which is formed by the space between the interior of the main die housing/air plate of the die and the exterior of the nozzle. The air forming chamber surrounds at least the lower portion of the nozzle and extends into the air plate assembly where it terminates in an annular fluid outlet port. The fluid outlet port typically has a diameter ranging from 3 to 5 mm. It is this fluid outlet port which forms the primary means for attenuating and fiberizing the fibers. As the fluid outlet port is reduced in diameter the fiberization/attenuation air is increased in velocity causing the fibers to be attenuated more severely.

To further attenuate and fiberize the molten fibers, a secondary fiberization means may also be used. The air plate assembly may be fitted with a secondary fluid outlet port spaced radially and axially outward from the first or primary fluid outlet port to create a plurality of secondary fluid streams which impinge upon and further fiberize the molten resin into fibers. The secondary fluid outlet ports are in fluid communication with the air supply via fluid channels which connect the secondary fluid outlet ports with the air forming chamber. The air forming chamber has a cavity surface which has a substantially cylindrical portion having a substantially annular shape when viewed in cross-section and a second frustoconical portion located within the air plate. The frustoconical portion is inclined as what is termed the primary fluid flow angle. This is the angle at which the primary fiberization fluid is directed at the flow of molten resin which is traveling along a first axis. The primary fluid flow angle is the angle between the vertical or first axis of the nozzle and lie tangent to the surface of the first frustoconical portion. Generally, the primary fluid flow angle should be between about 15° and 60°. Also note that this first axis defines the initial flow path of the molten resin as it exits the resin outlet orifice. The air plate assembly may be equipped with secondary fluid outlet ports spaced radially and axially outward from the first or primary fluid outlet port to create a plurality of secondary fluid streams which impinge upon and further fiberize the molten resin into fibers. The secondary fluid outlet ports are in communication with the air supply via fluid channels which connect the secondary fluid outlet ports with the air forming chamber. The secondary fluid outlet ports are angled radially inward towards the longitudinal axis of the nozzle so that the secondary fiberization fluid impinges upon the preliminary formed fibers at a predetermined angle. This angle is called the secondary fluid flow angle and is measured as the interior angle between the first axis of the resin flow (also the longitudinal axis of the nozzle) and lie tangent to any one of the fluid streams emanating from the secondary fluid outlet port.

The concave bottom surface of the air plate in combination with the primary and secondary fiberization fluid flows provides a confined fiberization area wherein the primary fiberization fluid through the outlet port contacts and substantially surrounds the flow of resin from the resin outlet orifice. Next, the secondary fiberization fluid impinges upon the preliminary formed fibers. Upon exiting the die, the fiberization air exiting the primary and secondary fluid outlet ports behaves as a freely expanding jet. A very high level of turbulence is created with this type of jet expansion which causes the molten resin stream to be pulled and drawn in random directions, thereby attenuating and fiberizing the molten resin stream to a very high degree. The secondary fiberization streams impinge upon the spread of fibers formed by the primary fiberization fluid flow and at the point of collision of the two flows the fiberization fluid is redirected to produce a non-circular expanding jet.

As mentioned earlier, the die assembly further includes means for selectively stopping and starting the flow of resin and thus the formation of fibers. In multi-die configurations it is possible to cycle one, some or all of the nozzles on and off. As a result, it is possible to interrupt the fiber formation process, thereby creating individual discrete quantities of fibers. The on/off control means includes a pneumatic fixture which is connected to and therefore forms a part of the main die housing. Extending from the pneumatic fixture into the main flow body of the die is a plunger assembly or reciprocating stem having a distal tip which is located above the resin flow capillary. The stem has an unseated condition, wherein the tip is retracted into the main flow body and is therefore spaced away from the entrance to the capillary. The stem also has a seated condition wherein the stem is reciprocated to seat the tip against the entrance to the capillary. By seating the stem, a hydrostatic pressure is created in the capillary which helps dislodge any debris located therein and restricts the flow of the molten resin from the resin flow outlet.

The pneumatic fixture includes a pneumatic chamber including an upper chamber and a lower chamber. The stem includes an end portion extending into the pneumatic chamber. The end portion of the stem has a piston mounted thereon and fitted with seals to contact the walls of the chamber to form the upper and lower chambers. The chamber includes a pair of hydraulic fluid ports opening into the pneumatic chamber for supplying varying fluid pressure on each side of the piston within the pneumatic chamber, thereby reciprocating the stem between the seated (off) and unseated (on) conditions.

The main flow body includes a stem port with the stem extending through the stem port. The die also includes a high temperature resistant dynamic seal for allowing sliding engagement while perfecting a seal between the stem and the stem port to prevent the passage of molten resin through the ports.

Operation of the on/off mechanism involves selectively pressurizing either the upper chamber or the lower chamber of the pneumatic fixture. To turn the mechanism on and start the flow of molten resin from the resin outlet orifice, the pressure from the upper chamber is relieved through the fluid port and pressurized air is fed into the lower chamber via another fluid port. As a result of the pressure imbalance of either side of the piston, the piston moves further into the upper chamber unseating the tip of the stem from the capillary and thereby allowing the release of the molten resin from the main flow body through the resin outlet orifice. To turn off the mechanism, and interrupt the flow of molten resin the above procedure is reversed. Namely, the pressure from the lower chamber is decreased and the pressure in the upper chamber is increased, again, causing a pressure imbalance which forces the tip of the stem to seat against the capillary and cut off the flow of molten resin. Additionally, this action will create a sufficient hydrostatic pressure within the capillary to help dislodge any debris located therein.

EXAMPLES

Having thus described several of the equipment and process configurations possible with the present invention, several examples will be given to demonstrate the practical applications of the present invention. In each of the examples a fibrous nonwoven batt was formed using wood pulp fibers (fluff) as the first fiber 40 and essentially continuous thermoplastic reinforcing fibers as the second fiber 42. The fibrous webs so produced are suitable for use as absorbents in personal care products such as diapers, feminine pads, training pants and incontinence garments as well as other possible applications.

A tensile test was performed on the dry fibrous webs by measuring the peak load required to break a 7.6 cm by 15.2 cm sample on an Instron Microcon I, model #A 1026 A, made by Instron located in Canton, Mass. Tensile tests were also performed on a Thwing Albert Model #1450 MM 24, made by Thwing Albert of Philadelphia, Pa. The crosshead speed on both pieces of equipment was 5.1 cm per minute with a gauge length of 10.2 cm. Wet tensile strengths were obtained by injecting 20 ml of water into the center of the samples by means of a pipet or syringe after they were placed within the jaws of the test device and immediately before activation of the device. Reported tensile tests were measured in both the machine and cross-directions.

Example I

A nonwoven fabric containing 95.9 percent pulp fibers and 4.1 percent meltsprayed polypropylene fibers by weight was produced in accordance with the leading region method described above and illustrated in FIGS. 17 and 18. A primary air stream containing fiberized wood pulp (Kimberly Clark, Coosa Pines, CR2054) was directed into the chamber and constituted the first plurality of fibers. The fibers were introduced into the top of the forming chamber via a pulp fiberizer at a rate of 1.3 kg/min. The pulp was a mixture of 80% softwood and 20% hardwood fibers. Fiber lengths were in the range from 0.5 mm to 10 mm, with a length-to-maximum width ratio of about 10/1 to 400/1. The air stream velocity of the entrainment air ranged from 9.2–19.8 m/sec.

Polypropylene (Himont PF015) was extruded through a die containing eight nozzles or orifices at a rate of 41.6 g/min. which is equivalent to 5.2 g/min. per orifice at a processing temperature of 252° C. using the process and equipment of the previously mentioned patent application for "Process And Apparatus For Forming A Nonwoven Web". The polymer was attenuated into fibers by an annular airstream maintained at a temperature of 250° C. The polypropylene fibers, which constituted the second plurality of fibers, were essentially continuous in length with approximate diameters ranging from 1 to 60 microns. The polypropylene polymer was introduced through a slot in the leading region of the forming chamber (perpendicular to the airstream containing the first fibers) at a velocity of 44 m/sec. measured 2.6 cm from the die face. The die tip was located 3.8 cm outside the wall of the chamber and 11.4 cm vertically from the base of the chamber and approximately 14 cm from the forming wire. The die was positioned so that the nozzles wēre two across and four in height. Ambient air (entrainment air) was allowed to enter the slot along with the extruded polypropylene fibers.

The forming chamber dimensions were 15.2 cm in width, 61 cm in length and 55.9 cm in height. The composite web was collected on a 1.4 meter diameter forming drum rotating at a speed of 16.2 m/min to which a 30.5 cm to 40.6 cm water vacuum was applied to hold the web to the drum. The forming drum contained a perforated forming screen 15.2 cm in width and continuous in length around the circumference. Located within the forming drum were recessed pockets which were 15.2 cm in width, 30.5 cm in length and 2.54 cm deep. The pockets were spaced 25.4 cm apart about the circumference of the drum. A scarfing roll removed a portion of the first fibers from the third region of the material resulting in a web that contained a central pocket of higher basis weight between two ends (basesheets) of lower basis weight. See FIG. 4. The resulting material thickness was comprised of three layers or regions. The first region, which was deposited directly on the drum forming surface, was composed primarily of the first fibers. The second region was composed of a mixture of the first and second fibers and the third region was composed primarily of the first fibers. The measured composite properties were as follows:

| | |
|---|---|
| Basis Weight (pocket): | 622 grams/square meter (gsm) |
| Basis Weight (basesheet): | 270 grams/square meter (gsm) |
| % Pulp fibers by weight: | 95.9% |
| % Polypropylene fibers by weight: | 4.1% |
| Pocket | |
| Thickness: | 3.81 mm |
| Density: | 0.16 g/cm³ |
| Basesheet | |
| Thickness: | 2.8 mm |
| Density: | 0.096 g/cm³ |
| Basesheet | |
| MD Dry Tensile Strength: | 1415 g |
| MD Wet Tensile Strength: | 1393 g |
| CD Dry Tensile Strength: | 320 g |
| CD Wet Tensile Strength: | 224 g |

To be able to compare the wet and dry tensile strengths of the web material thus formed, a control material containing only wood pulp fibers was made. The control sample had the following properties:

| Pulp only control | |
|---|---|
| Basis Weight: | 276 gsm |
| % Pulp fibers: | 100.0% |
| % Polypropylene fibers: | 0.0% |
| Thickness: | 2.8 mm |
| Density: | 0.098 g/cm³ |
| MD Dry Tensile Strength : | 62 g |
| MD Wet Tensile Strength: | 144 g |
| CD Dry Tensile Strength: | 46 g |
| CD Wet Tensile Strength: | 118 g |

As can be seen, the dry tensile of the basesheet material according to the present invention (1415 g) was over twenty times that of the control (62 g) in the machine direction. The wet tensile strength (1393 g) was almost ten times that of the control (144 g) in the machine direction. In addition to this tremendous increase in wet and dry strength, note too that because of the unique forming process (three layers with the reinforcing layer in the middle), the material could be scarfed on either or both sides to further contour the product.

Example II

The same material described in Example I was produced with the addition of a particulate superabsorbent (Sanwet Superabsorber Polymer, IM-5000P from Hoechst Celanese of Portsmouth, Va.). The superabsorbent was added through a pipe 80 located in the front side 62 of the forming chamber 10, 34 cm above from the base of the forming chamber 10, see FIG. 17, at a rate of 149 g/min. The placement of the first and second fibers were the same as in Example I with the superabsorbent particles being deposited primarily within the third region of the resultant material. The nonwoven material was composed of 12.8% superabsorbent, 3.5% polypropylene fibers, and 83.7% wood pulp by weight. The forming chamber dimensions were the same as described in Example I.

Example III

A nonwoven fabric containing 97.2 percent pulp fibers and 2.8 percent polypropylene fibers by weight was produced in accordance with the Trailing region method described above and illustrated in FIGS. 14 and 15. A primary air stream containing fiberized wood pulp (Kimberly Clark, Coosa Pines, CR2054) was directed into the chamber and constituted the first plurality of fibers. The pulp was a mixture of 80% softwood and 20% hardwood fibers and was deposited into the top of the chamber at a rate of 3.6 kg/min. Fiber lengths were in the range from 0.5 mm to 10 mm, with a length-to-maximum width ratio of about 10/1 to 400/1. The air stream velocity was 31.3 m/sec. as measured at a location approximately 10 cm above the forming wire. The forming chamber dimensions were 76.2 cm in width, 55.2 cm in length and 53.3 cm in height.

The continuous polypropylene fibers (polypropylene PF015 from Himont USA, Inc. of Wilmington, Del.) were extruded through a 45.7 cm wide die containing 24 nozzles or orifices at a rate of 103.8 g/min which is equivalent to 4.3 g/min per orifice at a processing temperature of 249° C. using the process and equipment of the previously mentioned patent application for "Process And Apparatus For Forming A Nonwoven Web". The die was positioned so that the nozzles were 12 across and 2 in height. The polymer was attenuated into fibers by an annular airstream maintained at 243° C. The polypropylene fibers were essentially continuous in length with approximate diameters ranging from 1 to 60 microns. The polymer was introduced through a slot in the back side 64 of the forming chamber using attenuation air at a velocity of 19.3 m/sec. as measured approximately 10 cm from the face of the die. The die was located within the trailing region C of the forming chamber at a downward angle of 75 degrees from the horizontal and constituted the second plurality of fibers. The die tip was located flush with the wall of the chamber and 35.6 cm vertically from the base of the chamber. The composite web was collected on a 71.1 cm wide flat forming wire at a speed of 18.3 m/min to which a 30.5 cm water vacuum was applied to hold the web to the wire. The material formed on the wire had a width of 50.8 cm. The resulting material thickness was comprised of two layered regions as illustrated in FIG. 16. The first region, deposited directly on the forming surface contained primarily the first fibers. The second region contained a mixture of the first and second fibers. The measured composite properties were as follows:

| | |
|---|---|
| Basis Weight: | 399 grams/square meter (gsm) |
| % Pulp fibers by weight: | 97.2% |
| % Polypropylene fibers by weight: | 2.8% |
| Thickness: | 2.8 mm |
| Density: | 0.13 g/cm³ |
| MD Dry Tensile Strength: | 572 g |
| MD Wet Tensile Strength: | 740 g |
| CD Dry Tensile Strength: | 272 g |
| CD Wet Tensile Strength: | 381 g |

To be able to compare the wet and dry tensile strengths of the web material thus formed, a control material containing only wood pulp fibers was made. The control sample had the following properties:

| Pulp only control | |
|---|---|
| Basis Weight: | 392 gsm |
| % Pulp fibers by weight: | 100.0% |
| % Polypropylene fibers: | 0.0% |
| Thickness: | 3.6 mm |
| Density: | 0.11 g/cm$^3$ |
| MD Dry Tensile Strength: | 117 g |
| MD Wet Tensile Strength: | 206 g |
| CD Dry Tensile Strength: | 105 g |
| CD Wet Tensile Strength: | 181 g |

A comparison of the composite material according to the present invention with the pulp only control sample revealed that the composite structure had a dry tensile strength in the machine direction (572 g) which was five times that of the control (117 g). The wet tensile strength of the composite in the machine direction (740 g) was over three and one half times that of the pulp control (206 g).

Example IV

A nonwoven fabric containing 97.5 percent pulp fibers and 2.5 percent polypropylene fibers by weight was produced in accordance with the Leading plus Trailing region method described above and illustrated in FIGS. 5 and 6. A primary air stream containing fiberized wood pulp (Kimberly Clark, Coosa Pines, CR2054) was directed into the top of the chamber and constituted the first plurality of fibers. The pulp was a mixture of 80% softwood and 20% hardwood fibers and was deposited into the chamber at a rate of 3.7 kg/min. Fiber lengths were in the range from 0.5 mm to 10 mm, with a length-to-maximum width ratio of about 10/1 to 400/1. The air stream velocity was 31.3 m/sec. as measured at a location approximately 10 cm from the wire. The forming chamber dimensions were the same as described in Example III.

Polypropylene (Himont PF015) was extruded through two 45.7 cm wide dies each containing 24 nozzles or orifices. The polymeric flow rate through each die was 47.2 g/min which is equivalent to 2.0 g/min per orifice, at a processing temperature of 249° C. using the process and equipment of the previously mentioned patent application for "Process And Apparatus For Forming A Nonwoven Web". The polymer was attenuated into fibers by an annular airstream maintained at 243° C. The polypropylene fibers were essentially continuous in length with approximate diameters ranging from 1 to 60 microns. A first die introduced polypropylene into the chamber through a slot located in the leading region. A and constituted the second plurality of fibers. A second die introduced polypropylene into the chamber through a slot located in the trailing region and constituted the third plurality of fibers. Both dies were angled toward the forming surface at a downward angle of 75 degrees from the horizontal using attenuation air at a velocity of 19.3 m/sec. as measured approximately 10 cm from the die face. The nozzles on each die were positioned 12 across and 2 in height and were located flush with the wall of the chamber and 35.6 cm vertically from the base of the chamber. The chamber was positioned 3.8 cm above the forming wire. The composite web was collected on a flat forming wire at a speed of 18.3 m/min. to which a 30.5 cm water vacuum was applied to hold the web to the wire. The forming wire was 71.1 cm wide and of continuous length and the formed material thereon had a width of 50.8 cm. The resulting material thickness was comprised of three layered regions as illustrated in FIG. 7. The first region, deposited directly on the forming surface, contained a mixture of the first and second fibers. The second region contained primarily the first fibers. The third region contained a mixture of the first and third fibers. The measured composite properties were as follows:

| | | |
|---|---|---|
| Basis Weight: | 406 | grams/square meter (gsm) |
| % Pulp fibers by weight | 97.5% | |
| % Polypropylene fibers by weight: | 2.5% | |
| Thickness: | 3.3 | mm |
| Density: | 0.12 | g/cm$^3$ |
| MD Dry Tensile Strength: | 763 | g |
| MD Wet Tensile Strength: | 822 | g |
| CD Dry Tensile Strength: | 390 | g |
| CD Wet Tensile Strength: | 377 | g |

Example V

A nonwoven fabric containing 98 percent pulp fibers and 2 percent meltsprayed polypropylene fibers by weight was produced in accordance with the Leading plus Trailing region method described above and illustrated in FIG. 8. A primary air stream containing fiberized wood pulp (Kimberly Clark, Coosa Pines, CR2054) was directed into the chamber and constituted the first plurality of fibers. The pulp was a mixture of 80% softwood and 20% hardwood fibers and was deposited into the top of the chamber at a rate of 3.7 kg/min. Fiber lengths were in the range from 0.5 mm to 10 mm, with a length-to-maximum width ratio of about 10/1 to 400/1. The air stream velocity was 31.3 m/sec. as measured approximately 10 cm above the forming wire. The forming chamber dimensions were the same as described in Example III.

Polypropylene (Himont PF015) was extruded through two 45.7 cm wide dies each containing 24 nozzles or orifices. The polymeric flow rate through each die was 37.4 g/min which is equivalent to 1.6 g/min per orifice, at a processing temperature of 249° C. using the process and equipment of the previously mentioned patent application for "Process And Apparatus For Forming A Nonwoven Web". The polymer was attenuated into fibers by an annular airstream maintained at 243° C. The polypropylene fibers were essentially continuous in length with approximate diameters ranging from 1 to 60 microns. The polypropylene fibers were introduced into the chamber through a slot located in the leading region A using one of the dies and constituted the second plurality of fibers. A second die introduced polypropylene fibers into the chamber through a slot located in the trailing region C and constituted the third plurality of fibers. Both dies were angled toward the forming surface at a downward angle of 12 degrees from the horizontal using attenuation air and at a velocity of 19.3 m/sec. as measured approximately 10 cm from the face of the die. The die tips were located 5.1 cm from the wall of the chamber and 40.6 cm vertically from the base of the chamber. The dies were positioned so that the nozzles were 12 across and 2 in height. Ambient air (entrainment air) was allowed to enter the slots along with the polypropylene fibers. The composite web was collected on a flat forming wire at a speed of 18.3 m/rain to which a 30.5 cm water vacuum was applied to hold the web to the wire. The forming wire was 71.1 cm wide and of continuous length and the formed material had a width of 50.8 cm. The resulting material thickness was comprised essentially of three regions, see FIG. 10. However, because both the second and third fibers were made of polypropylene, the polypropylene fibers were essentially mixed with the first fibers throughout the three regions. The measured composite properties were as follows:

| | |
|---|---|
| Basis Weight: | 403 grams/square meter (gsm) |
| % Pulp fibers by weight: | 98% |
| % Polypropylene fibers by weight: | 2% |
| Thickness: | 3.4 mm |
| Density: | 0.12 g/cm$^3$ |
| MD Dry Tensile Strength: | 858 g |
| MD Wet Tensile Strength: | 994 g |
| CD Dry Tensile Strength: | 526 g |
| CD Wet Tensile Strength: | 599 g |

Example VI

A nonwoven fabric containing 97 percent pulp fibers and 3 percent polypropylene fibers by weight was produced by injecting the second fibers into the sides of the forming chamber as illustrated in FIGS. 19 and 20. A primary air stream containing fiberized wood pulp (Kimberly-Clark, Coosa Pines, CR2054) was directed into the chamber and constituted the first plurality of fibers. The fibers were introduced into the top of the forming chamber via a pulp fiberizer at a rate of 7.3 kg/min and the pulp was a mixture of 80% softwood and 20% hardwood fibers. Fiber lengths were in the range from 0.5 mm to 10 mm, with a length-to-maximum width ratio of about 10/1 to 400/1. The air stream velocity of the entrainment air ranged from 9.2 m/sec. to 19.8 m/sec. The forming chamber dimensions were 40 cm in width, 61 cm in length, and 55.9 cm in height.

Polypropylene (Himont PF015) was introduced through two separate dies each containing eight nozzles or orifices. The nozzles on each die were positioned four across and two in height. The polymeric flow rate through each die was 113 g/min which is equivalent to 14.2 g/min per orifice and at a processing temperature of 263° C. using the process and equipment of the previously mentioned patent application "Process And Apparatus For Forming A Nonwoven Web". The polymer was attenuated into fibers by an annular airstream maintained at 258° C. Each die was located on a sidewall of the chamber in the leading region A so that the two polypropylene streams were directed towards one another perpendicular to the direction of the movement of the forming drums. The die tips were located 16.5 cm from the leading edge of the chamber and 36.8 cm above the bottom of the leading edge of the chamber. The dies were angled downwardly towards the wire at an angle of 30 degrees from the horizontal. The composite web was collected on a forming drum rotating at a speed of 77.5 m/min. to which a 30.5 cm to 40.6 cm water vacuum was applied to hold the web to the drum. The resulting material thickness was comprised of two layers or regions. The first region was deposited directly on the forming surface and was composed of a mixture of the first and second fibers. The second region was composed primarily of the first fibers. The basis weight of the material was 600 gsm.

Having thus described the invention in detail, it should be appreciated that various other modifications and changes can be without departing from the spirit and scope of the following claims.

We claim:

1. A multicomponent nonwoven structure comprising:
    a layered fibrous nonwoven web having a first region and a second region and comprising a plurality of first fibers and a plurality of second fibers;
    wherein:
        said first region is comprised of a mixture of said first fibers and said second fibers;
        said second region is comprised predominantly of said first fibers; and
        said fibrous nonwoven web contains from 0.1 to 6% of said second fibers by weight.

2. The multicomponent nonwoven structure of claim 1 wherein the first fibers are cellulose fluff fibers ranging from approximately 0.5 to 10.0 millimeters in length and having a length-to-maximum width ration of about 10/1 to 400/1.

3. The multicomponent nonwoven structure of claim 1 wherein the second fibers are reinforcing fibers generally having continuous lengths and being made from a fiber forming resin.

4. The multicomponent nonwoven structure of claim 1 wherein the fibrous nonwoven web further comprises a particulate superabsorbent material.

5. A multicomponent nonwoven structure comprising:
    a layered fibrous nonwoven web having a first region and a second region and comprising a plurality of cellulose fluff fibers ranging from approximately 0.5 to 10.0 millimeters in length and a plurality of reinforcing fibers having continuous lengths and being made from a fiber forming resin;
    wherein:
        said first region is comprised of a mixture of said cellulose fluff fibers and said reinforcing fibers;
        said second region is comprised predominantly of said cellulose fluff fibers; and
        said fibrous nonwoven web contains from 0.1 to 6% of said reinforcing fibers by weight.

6. The multicomponent nonwoven structure of claim 5 wherein the fibrous nonwoven web further comprises a particulate superabsorbent material.

7. A multicomponent nonwoven structure comprising:
    a layered fibrous nonwoven web having a first region, a second region and a third region, said fibrous nonwoven web comprising a plurality of cellulose fluff fibers ranging from approximately 0.5 to 10.0 millimeters in length and a plurality of reinforcing fibers having continuous lengths and being made from a fiber forming resin;
    wherein:

said first and third regions are comprised predominantly of said cellulose fluff fibers;

said second region is comprised of a mixture of said cellulose fluff fibers and said reinforcing fibers; and said fibrous nonwoven web contains from 0.1 to 6% of said reinforcing fibers by weight.

8. The multicomponent nonwoven structure of claim 7 wherein the fibrous nonwoven web further comprises a particulate superabsorbent material.

9. A multicomponent nonwoven structure comprising:

a layered fibrous nonwoven web having a first region, a second region and a third region, said fibrous nonwoven web comprising:

a plurality of cellulose fluff fibers ranging from approximately 0.5 to 10.0 millimeters in length;

a plurality of reinforcing fibers having continuous lengths and being made from a fiber forming resin; and a particulate superabsorbent material;

wherein:

said first region is comprised of a mixture of said cellulose fluff fibers and said reinforcing fibers;

said second region is comprised predominantly of said cellulose fluff fibers;

said third region is comprised of a mixture of said cellulose fluff fibers and said superabsorbent material; and said fibrous nonwoven web contains from 0.1 to 6% of said reinforcing fibers by weight.

* * * * *

UNITED STATES PATENT AND TRADEMARK OFFICE
CERTIFICATE OF CORRECTION

PATENT NO. : 5,409,768

DATED : April 25, 1995

INVENTOR(S) : F. Lee Dukenson, F.P. Abuto, L.E. Chambers Jr., Edward Werner, Tony Wisniski It is certified that error appears in the above-identified patent and that said Letters Patent is hereby corrected as shown below:

Column 2, line 62, "work place, It" should read --work place. It--;

Column 2, line 65, "in part: because" should read --in part because--;

Column 3, line 8, "chamber.    While" should read --chamber. While--;

Column 6, line 7, "schematic: top" should read --schematic top--;

Column 21, line 57, " region. A" should read --region A--;

Column 23, line 7, "18.3/rain" should read --18.3m/min.--;

Column 23, line 64, " drums. The" should read --drum. The--.

Signed and Sealed this

Fourteenth Day of November, 1995

*Attest:*

BRUCE LEHMAN

*Attesting Officer*  *Commissioner of Patents and Trademarks*